United States Patent [19]

Sigelman

[11] Patent Number: 4,538,888
[45] Date of Patent: Sep. 3, 1985

[54] BINOCULAR OPHTHALMOSCOPE

[76] Inventor: Jesse L. Sigelman, 27 E. 65th St., New York, N.Y. 10021

[21] Appl. No.: 391,494

[22] Filed: Jun. 24, 1982

[51] Int. Cl.³ .............................................. A61B 3/10
[52] U.S. Cl. .................................... 351/205; 351/214; 351/245
[58] Field of Search ............... 351/205, 219, 211, 214

[56] References Cited

U.S. PATENT DOCUMENTS

| 2,757,574 | 8/1956 | Thorburn | 88/39 |
| 3,403,957 | 10/1968 | Wilkinson | 351/38 |
| 3,582,191 | 6/1971 | Cohen | 351/16 |
| 3,652,153 | 3/1972 | Gambs | 351/14 |

FOREIGN PATENT DOCUMENTS

| 0048181 | 9/1981 | European Pat. Off. |
| 2053502 | 6/1979 | United Kingdom |

OTHER PUBLICATIONS

Fincham, "A Combined Hand Slit Lamp and Binocular Microscope", *The Optician*, Jan. 29, 1960, pp. 58–59.
The Exeter Indirect Ophthalmoscope, catalog sheet.
Mentor Slit Lamps, catalog sheet.
Kowa SL-2 and SL-5 Slit Lamp Microscope, catalog sheet.

*Primary Examiner*—Rodney B. Bovernick
*Assistant Examiner*—P. M. Dzierzynski
*Attorney, Agent, or Firm*—Sprung Horn Kramer & Woods

[57] ABSTRACT

A binocular ophthalmoscope of the type including an optical viewing system. The binocular ophthalmoscope includes a headgear adapted to be worn on the examiner's head for supporting the optical viewing system in optical alignment with the examiner's eyes and light source for illuminating a patient's eye which is slideably mounted on the headgear and movable in a lateral direction.

7 Claims, 10 Drawing Figures

BINOCULAR OPHTHALMOSCOPE

BACKGROUND OF THE INVENTION

This invention relates to an apparatus for examination of the eye, and in particular, to such an apparatus adapted for examination of the retina, vitreous, pigment epithelium, choroid, cornea, anterior chamber, iris, crystalline lens and anterior vitreous of the human eye. More specifically, this invention relates to a binocular ophthalmoscope having head gear to be worn on an examiner's head for supporting an optical viewing system and a light source for illuminating a patient's eye. The light source is laterally movable to permit illumination of the patient's eye from various angles with respect to the optical viewing system. The viewing system may be a binocular indirect ophthalmoscope which is used in conjunction with a hand held condensing lens to view an aerial or indirect image of the eye; a binocular biomicroscope for a direct microscopic view of the eye; or a binocular biomicroscope which is used together with a hand held condensing lens, for viewing an enlarged aerial image of the eye. The laterally movable light source is adapted to provide both slit beam and full beam illumination of the patient's eye.

The invention may be used to provide a fullbeam illuminated view to conduct examination of the fundus for retinal mapping or for full field viewing of the cornea, anterior chamber, iris, crystalline lens or vitreous. The invention may be used to provide a centered or angulated slit directly illuminated view of the retina and of the vitreous to detect vitreous attachments, retinal discontinuities, tumors of the choroid or pigment epithelium. Additionally, the invention may be used to provide a centered or angulated slit retro-illuminated view of the retina and vitreous gel to provide, in effect, a "back lighted" view of the posterior segment of the eye. Further, the invention permits the examiner to perform ophthalmoscopy of the vitreous and peripheral retina using simultaneously a slit beam light source together with manual scleral depression.

Binocular ophthalmoscopes of various types have been long known in the art, but their usefulness and flexibility have generally been restricted to use in examination of only a limited portion of the eye, or have involved the use of bulky equipment and of cumbersome and uncomfortable contact lenses on the patient's eye. None of these instruments permit a practical examination of the relationship of the peripheral retina to the vitreous. Further, none of these instruments permits a practical examination of the vitreous and peripheral retina by simultaneous use of slit beam illumination and scleral depression. For example, binocular indirect ophthalmoscopes of the type illustrated in U.S. Pat. No. 3,582,191 to Cohen; No. 3,963,329 to Stumpf et al.; and No. 2,757,574 to Thorburn may be used only to view the retina of the eye, are incapable of slit beam or retro illumination and cannot be used for examination of the diaphanous vitreous or other anterior portions of the eye. Conventional slit lamp biomicroscopes such as illustrated in U.S. Pat. No. 3,652,153 to Gambs or No. 3,403,957 to Wilkinson are incapable of examining the retina, vitreous body, posterior hyaloid, or other posterior portions of the eye without use of a Goldmann contact lens or an auxiliary mounted Hruby lens to eliminate corneal refraction. Both the Goldmann corneal contact lens and the mounted Hruby lens present significant disadvantages to the examination of a patient. The Goldmann contact lens is cumbersome and uncomfortable and requires anesthetization of the patient's cornea. Moreover, it may not conveniently be used with scleral depression which is required to bring the peripheral retina into view. The mounted Hruby lens has a very limited field of view permitting examination only of the posterior retina and optic nerve. Also, since the Hruby lens is fixed relative to the biomicroscope and the patient is generally stationary relative to the biomicroscope, the examiner cannot follow movement of the patient's eye and cannot view the retinal periphery with slit beam illumination.

SUMMARY OF THE INVENTION

The present invention overcomes the limitations associated with prior binocular indirect ophthalmoscopes and slit lamp biomiscroscopes by providing an apparatus which simply and conveniently permits examination of all portions of the eye, both anterior and posterior, including the posterior retina, peripheral retina, pigment epithelium, choroid, vitreous, cornea, anterior chamber, iris, crystalline lens, in full beam illumination, and angulated or centered slit direct illumination, or angulated or centered slit retroillumination.

Accordingly, it is an overall object of the present invention to provide a binocular ophthalmoscope which may be conveniently and flexibly utilized for a wide range of examinations of the human eye.

It is a further object of this invention to provide a head wearable binocular ophthalmoscope having a light source selectively providing both slit beam and full illumination of the patient's eye.

It is a further object of this invention to provide a head wearable binocular ophthalmoscope having a light source selectively providing both full and slit illumination of the patient's eye wherein such lamp is laterally movable to provide both centered and angulated slit illumination.

It is a further object of this invention to provide a head wearable binocular ophthalmoscope which selectively provides for the viewing of an inverted reversed aerial image of the eye, a full field nonaerial microscopic view of the eye, and a magnified aerial image of the eye.

It is yet a further object of this invention to provide, in combination, a head wearable binocular ophthalmoscope with a laterally movable attached light source permitting the examiner to perform ophthalmoscopy of the vitreous and peripheral retina using simultaneously a slit beam light source together with manual scleral depression.

In accordance with the present invention, there is provided a binocular ophthalmoscope having an interchangeable optical viewing system, a head gear adapted to be worn on an examiner's head supporting the viewing system in optical alignment with the examiner's eyes, and a selective full or slit beam light source mounted on the headgear and laterally moveable for direct or angulated illumination of a patient's eyes. In a particular illustrative embodiment demonstrating objects and features of the present invention, the viewing system is a conventional binocular indirect ophthalmoscope which may be interchanged with a conventional binocular biomicroscope. The viewing system can be constructed to optically function at any convenient desired working distance, typically of from approximately 4 inches to approximately 30 inches. The light source is slideably affixed to the head gear on a slide bar. The light source includes a provision for interchangeable aperture slides for either full or slit beam illumination.

BRIEF DESCRIPTION OF THE DRAWINGS

The above objects, aspects and advantages of the invention, as well as others, will be apparent from the detailed description of the preferred embodiment of the invention considered in conjunction with the drawings, which should be considered in an illustrative and not in a limiting sense, as follows.

DETAILED DESCRIPTION OF THE DRAWINGS

Figure 1:
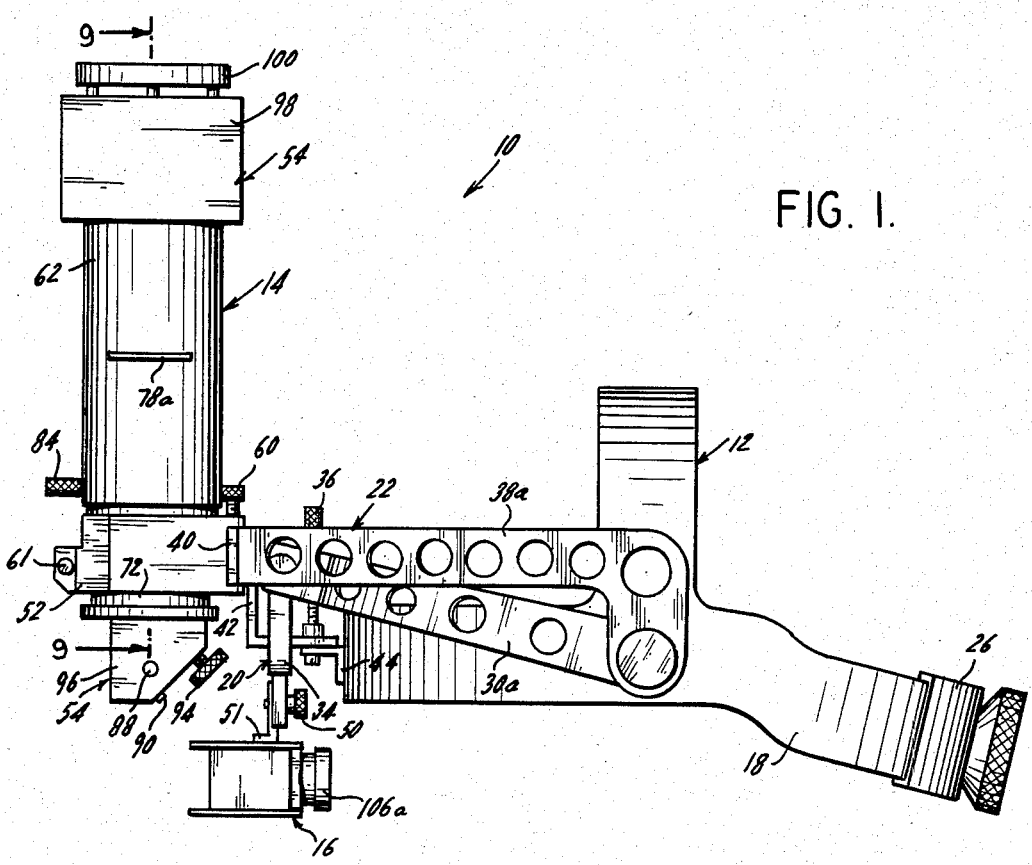
FIG. 1 is a side elevation view of a binocular ophthalmoscope in accordance with the present invention.

Referring to FIG. 1, a complete binocular ophthalmoscope is illustrated generally at 10. The binocular ophthalmoscope includes a head gear assembly generally indicated by 12, a light source assembly generally indicated by 14 and a viewing system generally indicated by 16.

Figure 2:
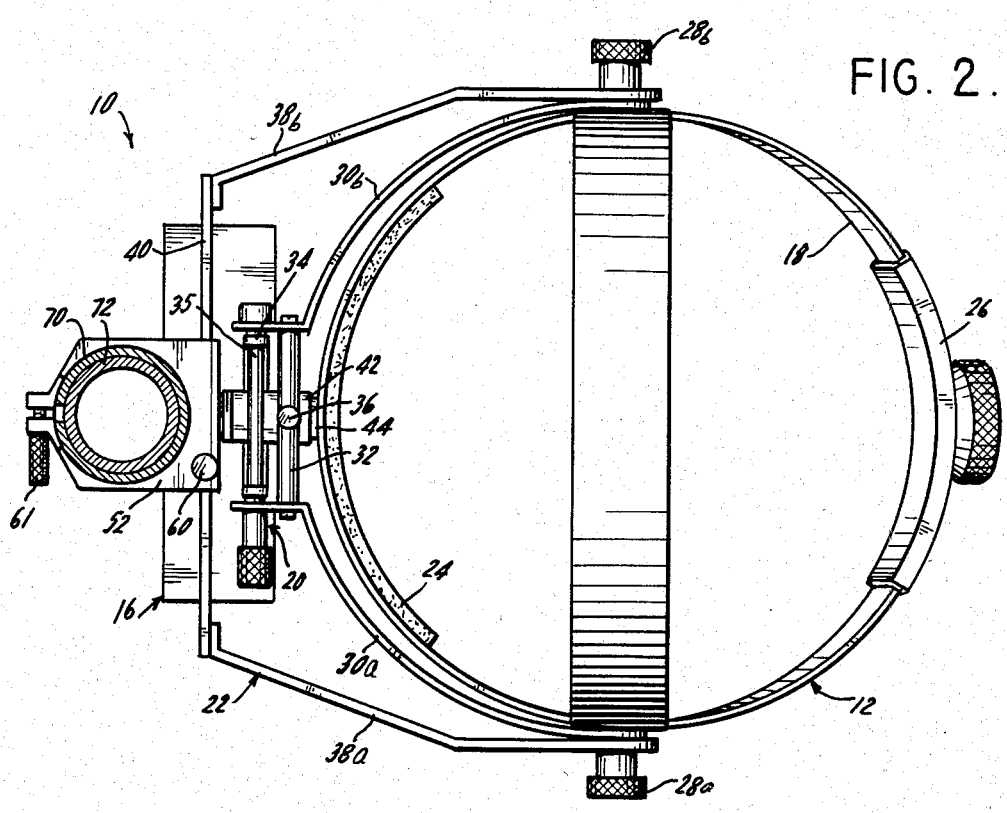
FIG. 2 is a top plan view of the binocular ophthalmoscope shown in FIG. 1.

Referring to FIGS. 1 and 2, it is seen that the head gear assembly 12 includes an adjustable head mount 18, a viewing system support 20 and a light source support assembly 22. The adjustable head mount 18 is provided with a resilient pressure pad 24 and an adjustment assembly 26. The viewing system support assembly 20 includes support arms 30a and b, a cross bar 32, having an integral threaded bore 48, a mounting bracket 34, a mounting bracket bar 35 and a height adjustment screw 36. The light source support assembly 22 includes support arms 38a and b, a slide bar 40 and a first and second angle brackets 42 and 44. The first and second angle brackets 42 and 44 are conventionally joined to each other to form a single support structure fixed at one end to the adjustable head mount 18. The viewing system support arm 30a and the light source assembly support arm 38a are pivotably coupled about a common axis to one side of the adjustable head mount 18 by a fastener 28a, while the viewing system support arm 30b and the light source assembly support arm 38b are pivotably coupled about a common axis to the opposite side of the adjustable head mount 18 by a fastener 28b.

Figure 4:
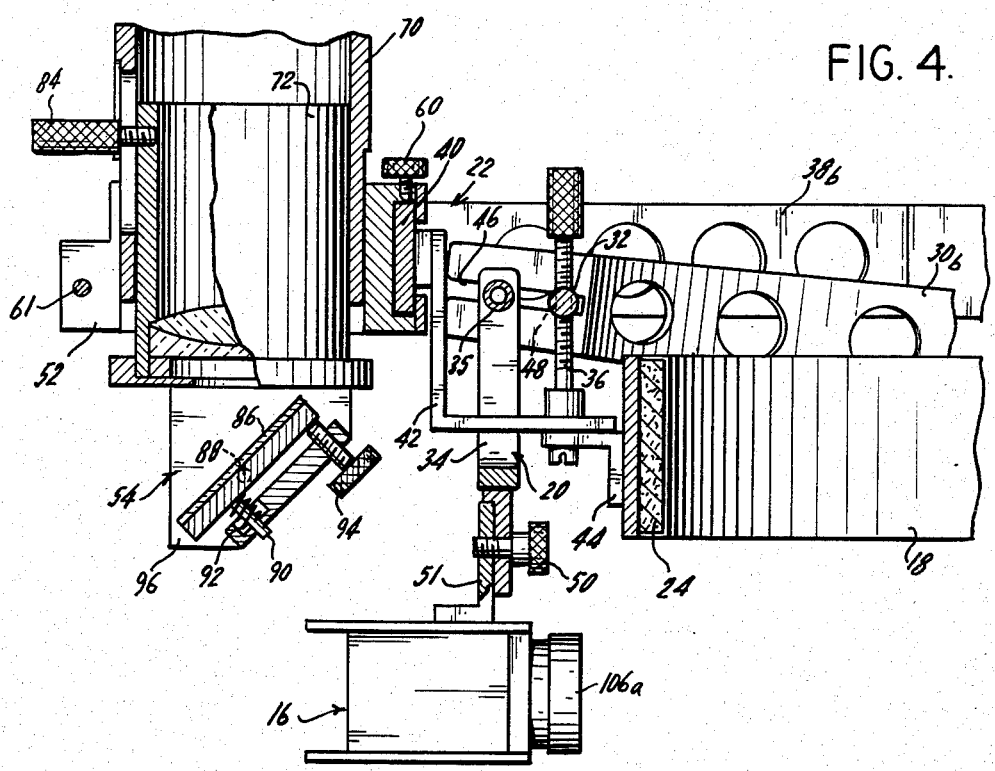
FIG. 4 is a sectional view of the binocular ophthalmoscope taken on line 4 of FIG. 3.

As best seen in FIGS. 2 and 4, the cross bar 32 and the mounting bracket bar 35 of the viewing system support assembly 20 are frictionally engaged within slots 46a and b of the viewing system support arms 30a and b, respectively. The height adjustment screw 36 engages the threaded bore 48 of the cross bar 32 and is rotatably mounted by conventional means at the junction of the first and second angle brackets 42 and 44. The mounting bracket 34 is secured by conventional means to the mounting bracket bar 35 so that the mounting bracket bar 35 together with the mounting bracket 34 may pivot within the slots 46a and b of the viewing system support arms 30a and b. A thumbscrew 50 is provided on the mounting bracket 34 for securing the viewing system 16 by its mounting bracket 51 to the viewing system support assembly 20. The slide bar 40 is supported at each end by the light source assembly support arms 38a and b and supported centrally by the first and second angle brackets 42 and 44.

Figure 3:
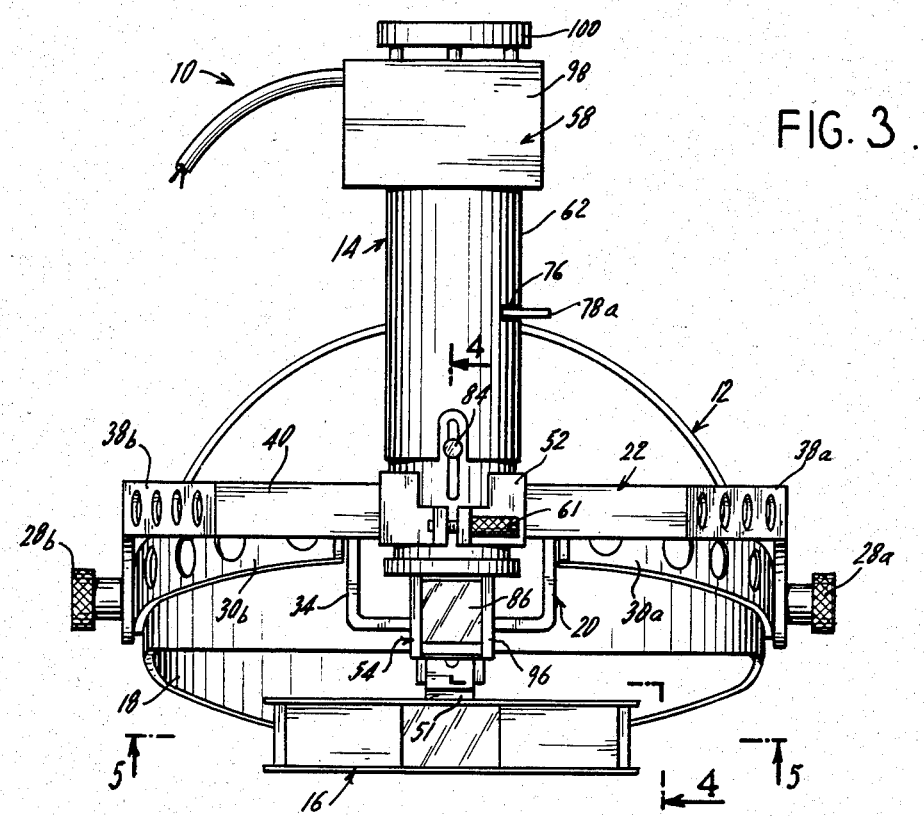
FIG. 3 is a front elevation view of the binocular ophthalmoscope shown in FIG. 1.
Figure 9:
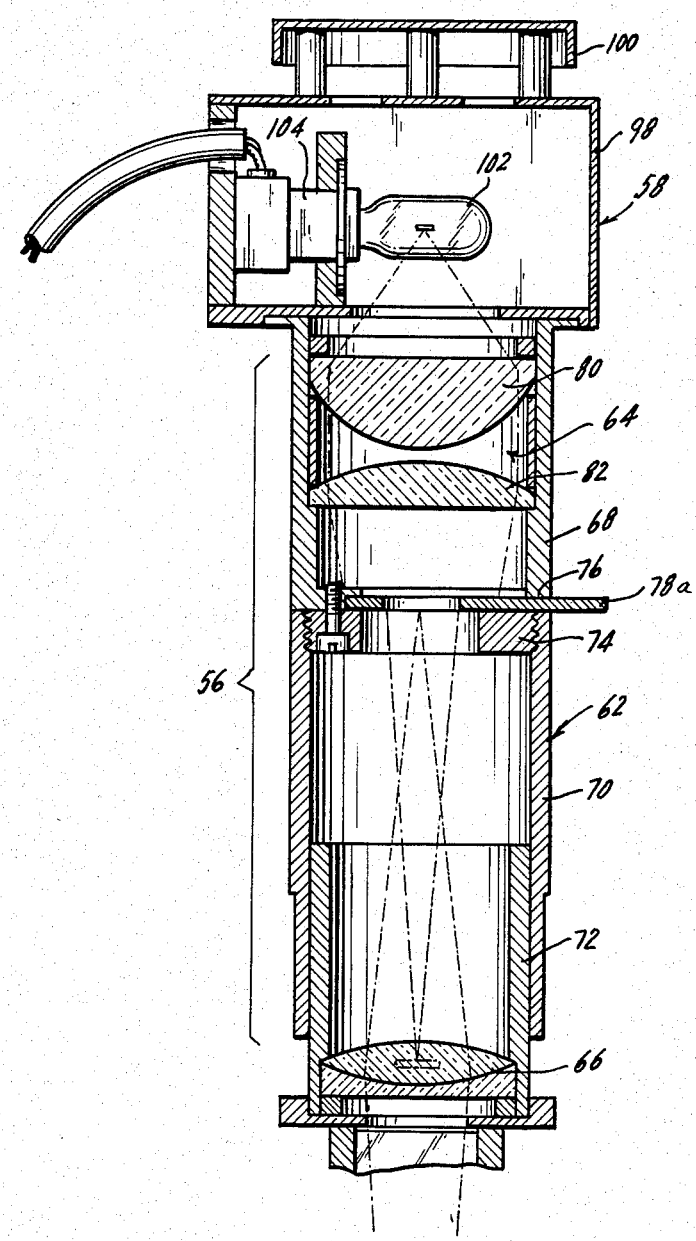
FIG. 9 is a sectional view of the light source assembly of the binocular ophthalmoscope taken on line 9—9 of FIG. 1.

As best seen in FIGS. 3, 4 and 9, the light source assembly 14 includes a light source mount 52, a mirror assembly 54, a lens assembly 56 and a lamp assembly 58. The light source mount 52 slideably engages with the slide bar 40 of light source support assembly 22 and is continuously movable along the length of the slide bar 40. The slide bar 40 is shown as being relatively straight, but may also be arc shaped. It has been found that the extent of longitudinal movement of the light source mount 52 and the light source assembly 14 on the relatively straight slide bar 40 should preferably subtend a distance of at least approximately two tenths of the maximum effective working distance of the viewing system 16. A locking screw 60 is provided to fix the light source mount 52 at any desired position along the slide bar 40. The lens assembly 56 is rotatably held within the light source mount 52 to permit aiming of the light source assembly 14 at the patient's eye at any position along the slide bar 40. If an arc shaped slide bar is used, the necessity for reaiming the light source assembly 14 to accomodate various positions along the slide bar can be minimized. A locking screw 61 is provided to secure the lens assembly 56 at the desired orientation within the light source mount 52.

Figure 10:
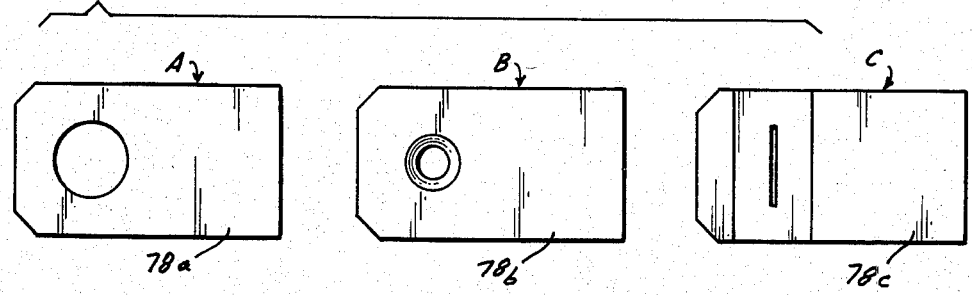
FIG. 10(A, B, C) is a plan view of alternate slides for insertion in the light source assembly shown in FIG. 9.

As best seen in FIGS. 9 and 4, the lens assembly 56 includes a three-piece housing assembly 62, a condenser lens system 64 and an objective lens 66. The housing assembly 62 includes first and second outer tubes 68 and 70, and inner tube 72 and an annular slide support 74. The annular slide support 74 is positioned and fixed in the second outer tube 70 at its juncture with the first outer tube 68. Proximate the annular slide support 74, the first outer tube 68 includes a slide notch 76 through which an aperture slide of suitable shape may be placed. Typical aperture slides 78a, b, and c are shown in FIG. 10(A-B-C) and aperture slide 78a is shown mounted within housing assembly 62 in FIG. 9. The condenser lens system 64 is mounted within the first outer tube 68 and includes first and second plano-convex lenses 80 and 82. Objective lens 66 is mounted within the inner tube 72 which in turn is slideably mounted within the second outer tube 70 to permit focusing. A locking screw 84 is provided to fix the inner tube 72 at a desired focused position. The mirror assembly 54 is mounted at the lower end of the inner tube 72 and includes a mirror 86, a pivot 88, a post 90, a spring 92, an angle adjustment screw 94 and a housing 96. The mirror 86 is adjustably mounted at an angle of approximately 45 degrees with respect to the axis of inner tube 72 and is secured on the pivot 88. The post 90 extends from the back of the mirror 86 through an aperture in the mirror housing 96 and is partially surrounded by the spring 92. One end of the spring 92 abuts against the mirror housing 96 and the other end abuts against the back of the mirror 86, thus providing stability to the mirror 86 in any adjusted position. The angle adjustment screw 94 is threaded through the mirror housing 96 so that it abuts against the back of the mirror 86. Rotation of the angle adjustment screw 94 permits fine adjustment of the angle of the mirror 86 about the pivot 88 so that the light produced by the light source assembly 14 can be aimed at the patient's eye.

The lamp assembly 58 is mounted on the upper end of the first outer tube 68 and includes a lamp housing 98, a vent cover 100, a lamp 102 and a lamp base 104. The lamp 102 is a conventional linear coil filament lamp, for example, Osram lamp No. 64260, and is mounted in the conventional lamp base 104 which is affixed to the lamp housing 98. The vent cover 100 forms a part of the lamp housing 98 immediately above the lamp 102 and is provided to dissipate, by convection, excess heat generated by the lamp 102.

Figure 5:
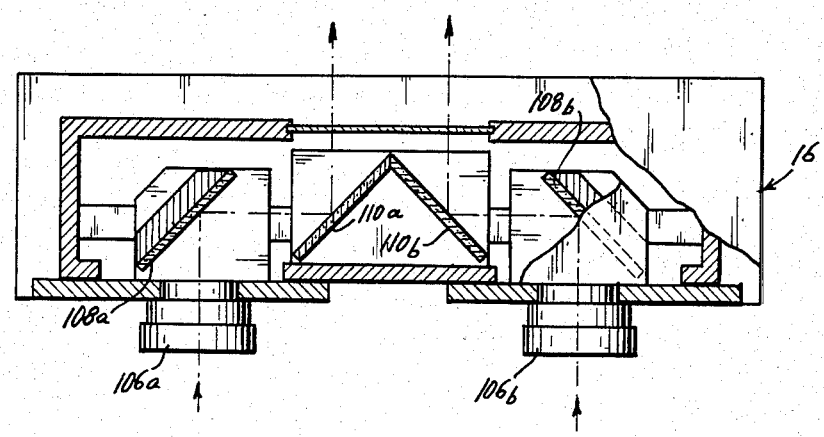
FIG. 5 is a sectional view of the viewing system of the binocular ophthalmoscope taken on line 5 of FIG. 3.

Referring to FIG. 5, the viewing system 16 is seen as a conventional binocular indirect ophthalmoscope having a pair of slideable viewing lenses 106a and b, cooperating with a pair of slideable mirrors 108a and b and a pair of fixed mirrors 110a and b. The slideable viewing lenses 106a and b and the slideable mirrors 108a and b are adapted to accommodate varying interpupillary distances of the examining physician's eyes. The slideable viewing lenses 106a and b are conventionally approximately 3 diopters. The fixed mirrors 110a and b function to reduce this interpupillary distance, thus permitting both of the examining physician's eyes to "look into" a patient's eye. The viewing system 16 is used in conjunction with a hand held condensing lens (not shown) of approximately 14 to 30 diopters to eliminate corneal difraction and provide an inverted reversed aerial image of the retina, vitreous jelly, pigment epithelium and choroid of the patient's eye.

Figure 6:
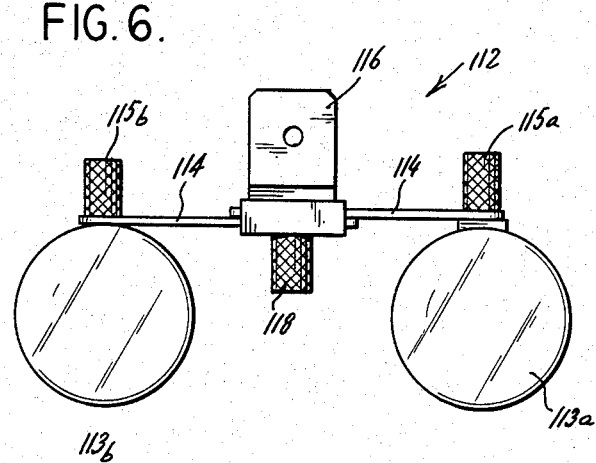
FIG. 6 is a front elevation view of an alternative viewing system for use in the binocular ophthalmoscope shown in FIG. 1.
Figure 7:
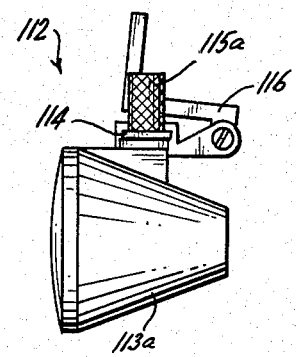
FIG. 7 is a side elevation view of the alternative viewing system shown in FIG. 6.
Figure 8:
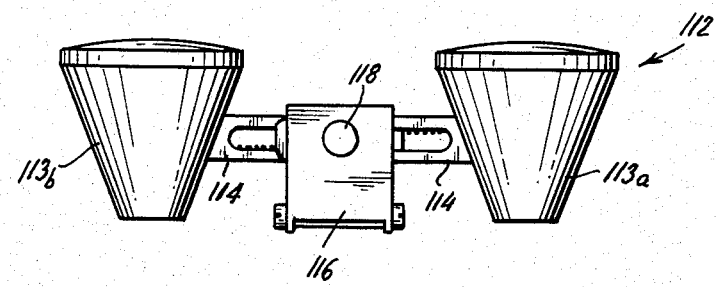
FIG. 8 is a bottom plan view of the alternative viewing apparatus shown in FIG. 6.

Referring to FIGS. 6, 7 and 8, an alternative binocular biomicroscope viewing system 112 is seen. The binocular biomicroscope 112 includes a pair of conventional compound microscope loupes 113a and b which are individually rotatably mounted on a sliding rack 114 in a conventional manner. The binocular biomicroscope viewing system 112 includes a hinged mount 11 for attachment to the viewing system support assembly 20. The sliding rack 114 is adjustable by rotation of a knob 118 to accommodate the interpupillary distance of the examiner's eyes, and the compound microscope loupes 113a and b individually rotate by turning knobs 115a and b for aiming at the patient's eye. The alternative binocular biomicroscope viewing system 112 provides a direct, nonaerial miscroscopic view of the anterior portion of the eye or, in conjunction with a hand held condensing lens (not shown) an enlarged aerial or indirect view of the posterior segment of the eye.

To commence an examination of a patient's eye by use of the binocular ophthalmoscope 10 of the present invention, the ophthalmoscope 10 is placed on the examiner's head so that the light source assembly 14 and viewing system 16 are facing forward, towards the patient. The examiner tightens the adjustable headmount 18 by use of the adjustment assembly 18, so that the headgear assembly 12 firmly rests upon the examiner's head. The examiner moves the viewing system 16 into optical alignment with his or her eyes by adjusting the height of the viewing system 16 through use of the height adjustment screw 36, adjusting the distance between the slideable viewing lenses 106a and b, and adjusting the distance between the viewing system 16 and the examiner's eyes by pivoting the viewing system 16 about the mounting bracket bar 34 within the slots 46a and b of the viewing system support arms 30a and b. The examiner then activates the lamp 102 of the light source assembly 14, places in the desired aperture slide 72a, b or c and focuses the light source assembly 14 by movement of inner tube 72 within second outer tube 70. When the desired focusing is achieved, locking screw 84 is tightened. By tilting his or her head, use of angle adjustment screw 94 and rotation of lens assembly 56 within light source mount 52, the examiner can aim the light produced by the light source assembly 14 at the patient's eye. An examination typically commences with a non angulated slit beam illuminated view of the patient's eye. For such an examination, the light source assembly is centered on the slide bar 40 and locked into place by the locking screw 60. Retro-illumination is achieved by aiming the light source assembly 14 so that the slit beam is slightly displaced from the portion of the eye being observed so that such portion receives only indirect lighting. Direct illumination is achieved by aiming the light source assembly 14 so that the slit beam is aimed directly at the portion of the eye being observed. A second portion of a typical examination entails viewing the eye by angulated slit illumination, either direct or retro. For such an examination, the light source assembly 14 is decentered and moved to a desired position on the slide bar 40. The aim of the light source assembly is adjusted by rotating the lens assembly 56 within the light source mount 52. Examination with full beam illumination or with the alternate viewing system 112 proceeds in essentially the same manner.

As is apparent from the foregoing specification, the present invention is susceptible of being embodied with various alterations and modifications which may differ particularly from those that have been fully described. For example, as is known in the art, it is possible to utilize a continuously variable slit rather than slides having various fixed slits. Laser light or colored incandescent light could replace the white incandescent bulb as the light source. For this reason, it is to be fully understood that all of the foregoing is intended to be merely illustrative and is not to be construed or interpreted as being restrictive or otherwise limiting of the present invention.

What I claim is:

1. An indirect binocular ophthalmoscope, comprising:

an optical viewing system;

light source means having a light outlet for illuminating a patient's eye; and headgear means mountable on an examiner's head during use for supporting the optical viewing system in optical alignment with the examiner's eyes and the light source means with the light outlet above the optical viewing system;

wherein the light source means includes a cylindrical housing, means for selectively providing both full beam and slit beam illumination of a patient's eye and wherein the headgear means includes means mounting the cylindrical housing for movement only in a lateral direction and for rotation about the axis of the housing independent of the lateral movement to alter the angle of the light beam from the light source means without changing its vertical angulation whereby the user can independently adjust the lateral position of the light beam and angle of the light beam independently and without affecting the vertical angulation.

2. The indirect binocular ophthalmoscope according to claim 1, wherein means mounting the cylindrical housing for rotation comprises means activated by one hand for releasably fixing the housing in a desired angular orientation.

3. The indirect binocular ophthalmoscope according to claim 1, wherein the means for providing both full and slit beam illumination comprises means forming a slit, a first condensing lens for focusing light on the slit and a second condensing lens for refocusing the light passing through the slit onto an aerial image of the retina.

4. The indirect binocular ophthalmoscope according to claim 1, wherein the light source means comprises a mirror at the light outlet and means independent of the means mounting the housing for rotation and for lateral movement for adjusting the tilt of the mirror to adjust the vertical angulation of the light beam.

5. The indirect binocular ophthalmoscope according to claim 2, wherein the light source means comprises a mirror at the light outlet and means independent of the means mounting the housing for rotation and for lateral movement for adjusting the tilt of the mirror to adjust the vertical angulation of the light beam.

6. The indirect binocular ophthalmoscope according to claim 2, wherein the means for providing both full and slit beam illumination comprises means forming a slit, a first condensing lens for focusing light on the slit and a second condensing lens for refocusing the light passing through the slit onto an aerial image of the retina.

7. The indirect binocular ophthalmoscope according to claim 1, wherein the headgear means comprises, a first band for encircling the head, a second band connected to the first band for resting on the top of a head during use, a first pair of arms connected at one end to the first band, means mounting the light source means for lateral movement connected to the other end of the first pair of arms and to the first band, a second pair of arms pivotally connected at one end to the first band and for supporting the optical viewing system and means for adjustably pivoting the second pair of arms relative to the first band to adjust the vertical position of the optical viewing system.

* * * * *